US009427234B2

(12) United States Patent
Lund-Clausen et al.

(10) Patent No.: US 9,427,234 B2
(45) Date of Patent: Aug. 30, 2016

(54) IMPLANTABLE OCCLUDER OR FILTER

(71) Applicant: COOK MEDICAL TECHNOLOGIES LLC, Bloomington, IN (US)

(72) Inventors: Jacob Lund-Clausen, Herlev (DK); Per Hendriksen, Herlufmagle (DK); Nicholas Gulmann Lundsteen, Hvalsoe (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 638 days.

(21) Appl. No.: 13/802,893

(22) Filed: Mar. 14, 2013

(65) Prior Publication Data

US 2013/0338491 A1 Dec. 19, 2013

(30) Foreign Application Priority Data

Jun. 13, 2012 (GB) .................................. 1210464.2

(51) Int. Cl.

*A61B 17/12* (2006.01)
*A61F 2/01* (2006.01)
*A61B 6/12* (2006.01)
*A61B 17/00* (2006.01)

(52) U.S. Cl.

CPC ... *A61B 17/12109* (2013.01); *A61B 17/12031* (2013.01); *A61B 17/12036* (2013.01); *A61B 17/12172* (2013.01); *A61B 17/12177* (2013.01); *A61B 6/12* (2013.01); *A61B 2017/00867* (2013.01); *A61B 2017/1205* (2013.01); *A61F 2/01* (2013.01)

(58) Field of Classification Search

CPC .................. A61B 17/12109; A61B 17/12172; A61B 17/12031; A61B 17/12036; A61B 17/12022; A61B 17/12099–17/12122

USPC ......... 128/830–838, 842, 843; 606/135, 191, 606/200; 623/1.24–1.26, 2.1, 2.11

See application file for complete search history.

(56) References Cited

U.S. PATENT DOCUMENTS 5,382,261 A 1/1995 Palmaz
5,935,137 A * 8/1999 Saadat et al. ................. 606/135
6,254,633 B1 * 7/2001 Pinchuk et al. ............... 623/1.3
2002/0177872 A1 11/2002 Papp et al.
2003/0070682 A1 4/2003 Wilson et al.
2003/0212429 A1 11/2003 Keegan et al.
2006/0004434 A1 1/2006 Forde et al.
2006/0041269 A1 * 2/2006 Horrigan ....................... 606/198
2006/0106361 A1 * 5/2006 Muni et al. ................... 604/500
2007/0056591 A1 * 3/2007 McSwain ...................... 128/831
2009/0216263 A1 8/2009 Tekulve

FOREIGN PATENT DOCUMENTS

WO WO 2004/010845 A2 2/2004
WO WO 2009/124247 A2 10/2009
WO WO 2009124247 A2 * 10/2009 ............ A61B 17/12

* cited by examiner

*Primary Examiner* — Todd E Manahan
*Assistant Examiner* — Charles Wei
(74) *Attorney, Agent, or Firm* — Brinks Gilson & Lione

(57) ABSTRACT

An occlusion device (10) includes a cannula (24), a dilator tip (20) fixed to the cannula and a frame member formed of an occlusion member (28) and a sleeve (30). The occlusion member (28) is covered with occlusion material (26). The cannula (24) is in the form of a tube having a lumen (25) passing therethrough. The dilator tip (20) also has a lumen therethrough and a valve (32). The arrangement is such that the occluder (10) can be delivered by an over the wire method using a guide wire, whereupon the cannula and dilator tip remain in the patient as part of the occluder assembly (10).

21 Claims, 4 Drawing Sheets

24 30 26 28 40 22
14 12 20 32

IMPLANTABLE OCCLUDER OR FILTER

CROSS-REFERENCE TO RELATED APPLICATIONS

This application is related to and claims the benefit of priority to GB 1210464.2, filed on Jun. 13, 2012 which is incorporated herein by reference in its entirety.

TECHNICAL FIELD

The present invention relates to an implantable medical device for implanting into a vessel. In particular the invention relates to an implantable occlusion device which can be introduced over a guide wire.

BACKGROUND

Vascular occlusion devices (hereinafter generally referred to as "occlusion devices") are surgical implements or implants that are placed within the vascular system of a patient. There are a number of reasons why it may be desirable to occlude a vessel. For example, the site of a stroke or other vascular accident can be treated by placing an occlusion device proximal of the site to block the flow of blood to the site, thereby alleviating leakage at the site. An aneurysm can be treated by the introduction of an occlusion device through the neck of the aneurysm. Other diseases, such as tumours (whether benign or malignant) can be treated by occluding the flow of blood to a targeted site of interest.

Several known occlusion devices include a coil having fibres, threads or strands attached to the coil; others include detachable balloons. In order to occlude a vessel successfully, occlusion devices must not have any substantial openings in them through which fluid can flow. Due to their structures, such occlusion devices are conventionally delivered without the assistance of a guide wire, which can be disadvantageous primarily due to less efficient deployment procedures.

Examples of known occlusion devices are disclosed in WO2009/124247, US2009/0216263, U.S. Pat. No. 5,382,261 and US2006/0004434.

DISCLOSURE OF THE INVENTION

According to an aspect of the present invention, there is provided an implantable medical device for implanting into a vessel, the implantable medical device including: an expandable frame member for at least partially obstructing a vessel; a cannula element including a first lumen for receiving a guide wire, said cannula element being coupled within the frame member; a dilator tip including a second lumen for receiving a guide wire, said dilator tip being coupled to an end of the cannula element; wherein one of the cannula element and the dilator tip is provided with a sealing element for sealing one of the first lumen and the second lumen.

Where the cannula element is provided with a sealing element the first lumen may be sealable by the sealing element. Where the dilator tip is provided with a sealing element the second lumen may be sealable by the sealing element.

By at least partially obstructing a vessel the expandable frame member at least partially obstructs passage through the vessel of an object, for example.

The first and second lumens for receiving a guide wire are aligned with one another and are preferably substantially coaxial.

The sealing element may comprise a valve, for example a cross-slit valve.

The frame member may provide a collapsed introduction configuration wherein the frame member lies substantially parallel to the cannula element. The frame member may comprise first and second portions, each extending longitudinally along the cannula element away from the other.

The frame member may provide an expanded deployed configuration wherein the frame member extends radially from the cannula element. In the deployed configuration the frame member may extend radially from and longitudinally along the cannula element so as to form a substantially conical shape. In the deployed configuration the first and second portions may each extend radially from and longitudinally along the cannula element away from one another so as to form a substantially hourglass shape.

The frame member may comprise a central sleeve. The frame member may comprise an obstruction member extending from the central sleeve and moveable from an introduction position to a deployed condition so as to at least partially obstruct a vessel. The obstruction member may be the first and second portions of the frame member. The obstruction member may partially or totally obstruct passage through a vessel in use.

The implantable medical device may be at least one of an occlusion device and a filter. Where the medical device is a filter, the obstruction member may partially obstruct the vessel by preventing free flow of objects, for example, through the vessel, but allowing fluid to flow through the device.

Where the medical device is an occlusion device the obstruction member may be covered with occlusion material. Such occlusion material may comprise at least one of silicone, polyurethane, Dacron®, Thoralon®, ePTFE, polyethylene terephthalate, and polyethylene. Where the medical device is an occlusion device it may completely obstruct passage through a vessel so as to occlude the vessel.

The cannula element may be attached to the central sleeve of the frame member. For example, the cannula element may be coupled within the central sleeve of the frame member. The cannula element may be coupled concentrically within the central sleeve of the frame member.

The cannula element and central sleeve may be attached, for example, by heat-shrinking, friction, gluing, or using a barb arrangement, such as a barb on one member and a cooperating hole on the other member. Other known fixing means and arrangements may be used.

The cannula element may have a tapered outer diameter, said outer diameter ranging from smaller than a diameter of the central sleeve to greater than a diameter of the central sleeve, such that the relative positions of the cannula and central sleeve can be fixed by forcing the cannula into the central sleeve.

The cannula may be fixed within the central sleeve by friction, for example by providing ribs on the cannula, or by shrink fitting the sleeve around the cannula.

The central sleeve may be provided with at least one inwardly extending barb for fixing the location of the central sleeve relative to the cannula element. The central sleeve may be made from a shape memory material, polymer or alloy, and preferably a nickel titanium alloy such as Nitinol.

The cannula element may comprise one of a cannula, a catheter, and a tube. The cannula element may be made from, for example, at least one of a plastics material or a metal or metal alloy, for example titanium or titanium alloy such as Nitinol.

The medical device may comprise at least one radiopaque marker. The medical device may comprise at least one barb for fixing the occlusion device in position in the vessel. The medical device may comprise both at least one of a radiopaque marker and at least one barb for fixing the occlusion device in position in the vessel. The barb may be provided on the radiopaque marker.

The cannula element and the dilator tip may comprise a single member.

The cannula element and the dilator tip may be fixed to one another.

BRIEF DESCRIPTION OF THE DRAWINGS

Preferred embodiments of the present invention are described below, by way of example only, with reference to the accompanying drawings, in which.

DESCRIPTION OF THE PREFERRED EMBODIMENTS

It is to be understood that the drawings are schematic only and are not intended to be representative of dimensions or proportions of the various elements shown therein. In some instances, dimensions, sizes and proportions have been modified in order to assist in the visualisation of various features of the elements shown, that is for the purpose of explanation only. The person skilled in the art will be aware of the appropriate dimensions and proportions having regard to common knowledge in the art.

In this description, when referring to an introducer or deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as an occlusion device, the term proximal refers to a location that in use is closest to the patient's heart, and the term distal refers to a location furthest from the patient's heart.

Figure 1:
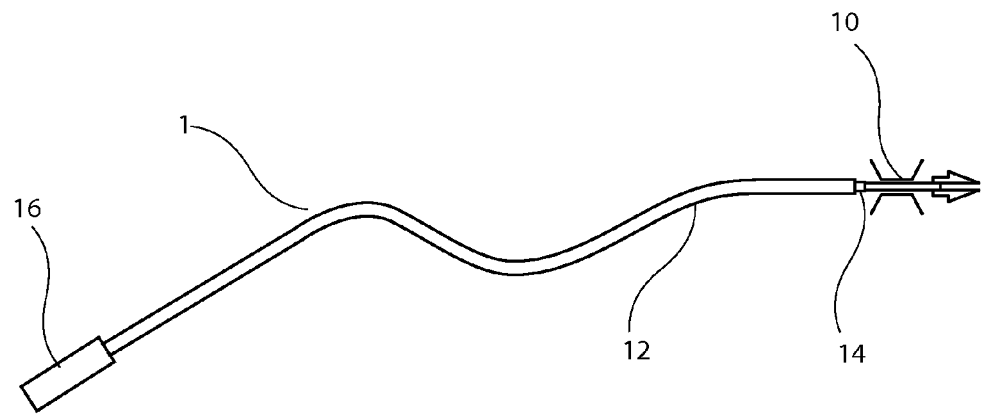
FIG. 1 is a schematic diagram of an occlusion device and introducer assembly according to an embodiment of the present invention.

FIG. 1 is a schematic diagram of an occlusion device 10 and introducer assembly 1. The introducer assembly 1 comprises an outer sheath 12, a pusher catheter 14 and a handle 16. Both the pusher catheter 14 and the outer sheath 12 may be introduced into a patient over a guide wire.

Figure 2:
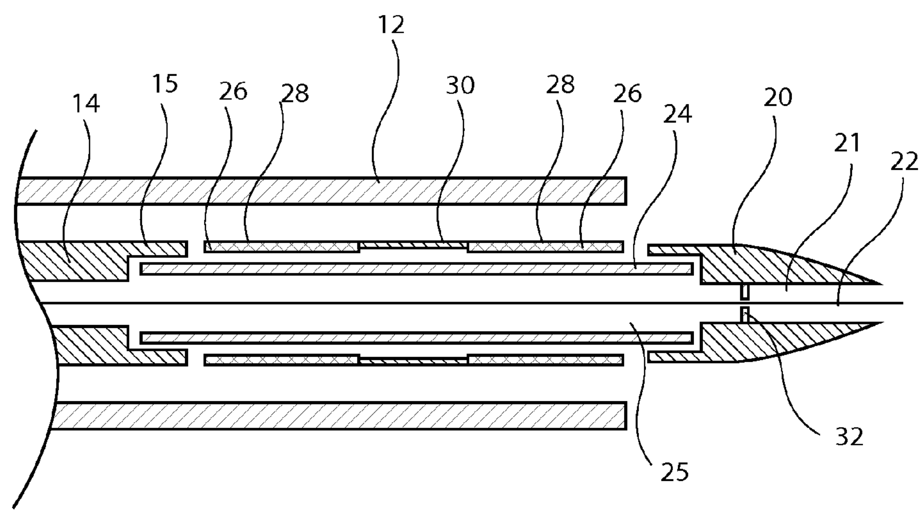
FIG. 2 is a cross-sectional view of an embodiment of an occlusion device as taught herein in an introduction configuration.

The occlusion device 10 is locked to the distal end of the pusher catheter 14 by a locking mechanism 15 (shown in FIG. 2). The handle 16 of the introducer assembly controls relative movement of the outer sheath 12 and pusher catheter 14, in order to expose the occlusion device and actuation of the locking mechanism on the pusher catheter 14 in order to release the occlusion device 10 from the introducer assembly 1. The handle 16 may also be operable to cover the occlusion device with the outer sheath 12 and to actuate the locking mechanism 15 to lock the occlusion device 10 to the distal end of the pusher catheter 14. The components of the handle assembly 16 may be of the type typical in such devices and are therefore not described herein in any detail. They may, in an embodiment, be as described in U.S. 61/072,903, the contents of which are incorporated herein by reference.

FIG. 2 is a cross-sectional sectional view of an embodiment of an occlusion device 10 as taught herein and an introducer assembly for delivering the occlusion device 10. In FIG. 2 the introducer and occlusion device 10 are shown in an introduction configuration. In the introduction configuration the occlusion device 10 is radially compressed and locked to the distal end of the pusher catheter 14, while the outer sheath 12 covers the occlusion device to protect it from damage and prevent early release.

The occlusion device 10 includes a cannula 24, a dilator tip 20 and a frame member formed of an occlusion member 28 and a sleeve 30. The occlusion member 28 is covered with occlusion material, in this case a graft material membrane 26. The cannula 24 is in the form of a tube having a lumen 25 passing therethrough. The dilator tip 20 is secured to the proximal end of the cannula 24 such that in use it is positioned at the distal end of the introducer assembly and therefore leads the way for the assembly through the patient's vasculature.

The central sleeve of the frame member comprises a tube having a lumen. During manufacture the cannula is placed within the lumen of the central sleeve and the sleeve is heat shrunk around the cannula to provide secure attachment of the components. In this way the central sleeve attaches the occlusion member to the cannula.

The occlusion member comprises two portions, a first portion extending from the proximal end of the central sleeve, and a second portion extending from the distal end of the central sleeve. When expanded the first and second portions have a cone shape and extend in opposing directions such that together they could be said to have an hourglass shape, expanding out and away from the central sleeve along the length of the cannula. On introduction the first and second portions are radially compressed around the cannula such that the occlusion member has a slim profile. The occlusion member is covered with occlusion material. When the occlusion device is expanded the occlusion member supports the occlusion material which occludes the vessel. It is to be understood that the occlusion material could in some embodiments be sufficient to cause occlusion of the vessel, that is by promoting local thrombosis of the vessel, although it is preferred that the material has a density sufficient to effect occlusion per se.

A seal 32 is provided in the lumen 21 of the dilator tip 20. In FIG. 2 the occlusion device has been passed over a guide wire, such that the guide wire is shown passing through the lumen 25 of the cannula 24 and through the lumen 21 of the dilator tip 20, and passing through the seal 32 in the dilator tip lumen 21.

The cannula 24 may be formed of a plastics material, such as polyether ether ketone (PEEK), a robust thermoplastics polymer which holds its shape well, maintaining the lumen 25 therethrough, so that the occlusion device may easily pass over a guide wire on introduction into a patient. As mentioned above, the cannula could be made of other materials including metal or metal alloy.

The dilator tip is a flexible molded tapered tip which is formed from a polymer such as polyurethane. The dilator tip guides the occlusion device and introducer assembly smoothly and easily through the patient's vasculature with the minimum of discomfort for and damage to the patient, as is known in the art.

The frame member, that is the occlusion member and the central sleeve, are preferably made from a material which can exhibit super-elastic properties, such as shape memory materials including Nitinol. The frame member is laser cut to provide the tube for the central sleeve and an occlusion member having struts arranged in diamonds. In this way the occlusion member can be easily compressed for delivery and can expand quickly and easily to its memory shape on withdrawal of the outer sheath. In addition, the sleeve member can be heat shrunk to securely attach the frame to the cannula.

The occlusion material covering the occlusion member may be a film of material. For example, the occlusion material may be silicone or graft material, providing a good barrier against fluid and occluding the vessel well. In other embodiments, the occlusion material could be natural material such as SIS. In a preferred embodiment the occlusion material is ePTFE as it is able to form an extremely thin film. The occlusion material may be, for example, molded to or adhered to the frame.

The seal 32 may be a cross slit valve, which allows a guide wire to pass therethrough while sealing around the guide wire to prevent or minimise fluid flow through the lumen of the occlusion member when deployed. When the guide wire is withdrawn from the device the seal 32 closes the passage through which the guide wire passed, sealing the device to substantially prevent fluid flow through the lumen of the occlusion member.

It is also envisaged that the valve 32 could be relatively rigid, in which case it will open and close by deformation of the dilator tip. More particularly, the walls of the dilator tip surrounding the valve, being elastic, can expand radially to open the valve when an element, such as a guide wire, is forced through the valve. The cross slit of the valve therefore opens by expansion of the dilator tip walls to allow a guide wire to pass through the valve. The valve seals around the guide wire to substantially prevent fluid flow through the lumen of the occlusion member during deployment of the occlusion device. When the guide wire is withdrawn from the device the elastic walls of the dilator tip relax back into their rest position and the seal 32 closes, closing the passage through which the guide wire passed and sealing the device to substantially prevent fluid flow through the lumen of the occlusion member.

Figure 3:
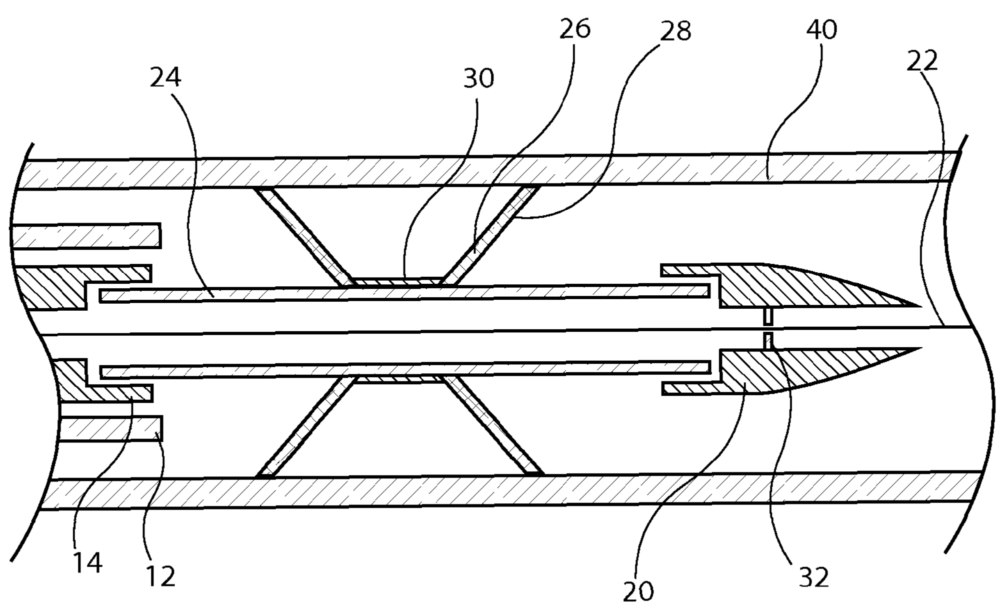
FIG. 3 is a cross-sectional view of the occlusion device shown in FIG. 2 during placement of the device in a vessel.
Figure 4:
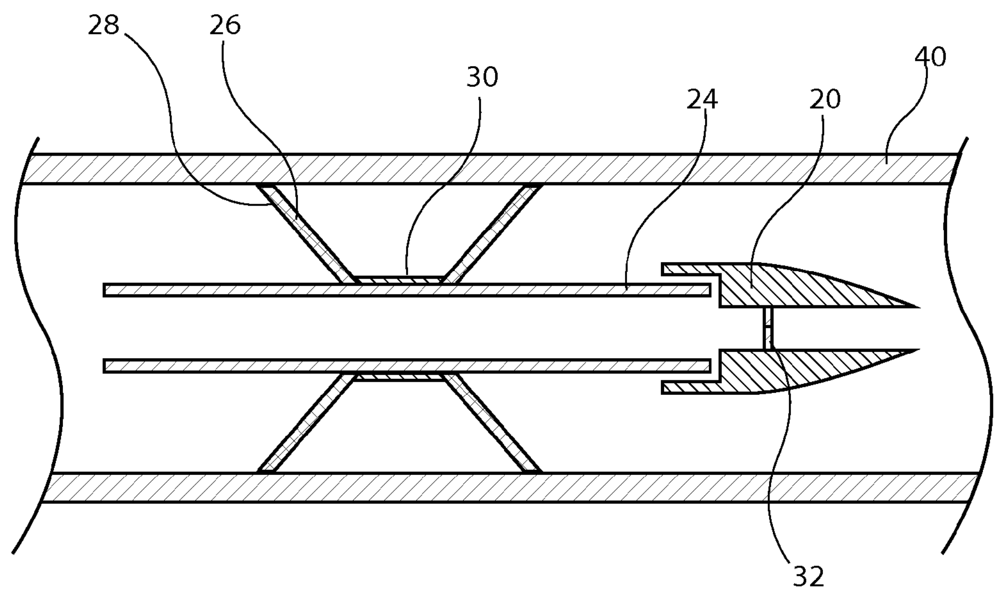
FIG. 4 is a cross-sectional view of the occlusion device of FIGS. 2 and 3 in a vessel after withdrawal of the guide wire and introducer assembly.

FIG. 3 is a cross-sectional view of the occlusion device 10 of FIG. 2 during placement of the device in a patient's vessel 40, and FIG. 4 is a cross-sectional sectional view of the occlusion device 10 of FIGS. 2 and 3 in the vessel 40 after placement of the device in a patient's vessel 40. In FIG. 3, the outer sheath 12 has been withdrawn from over the occlusion device 10 allowing the occlusion member 28 of the occlusion device 10 to expand to span the vessel. Fluid flowing through the vessel is blocked from flowing past the occlusion device by the material 26 covering the occlusion member 28 and from flowing through the lumen of the occlusion device by the guide wire and seal 32 in the lumen 21 of the dilator tip 20. The vessel is therefore occluded by the occlusion device 10.

In FIG. 4 the introducer assembly 1 and guide wire 22 have been withdrawn, leaving only the expanded occlusion device 10 in place in the vessel 40. The seal 32 closes shut on removal of the guide wire 22 to prevent fluid flowing through the lumen 21, 25 of the valve. As can be seen, the cannula 24 and dilator tip 20 remain a part of the occlusion device 10 and thus are not removed from the patient's vessel. It is this feature which enables the occlusion device to be delivered in an over-the-wire manner.

Deployment of the occlusion device is now described with reference to FIGS. 1 to 4. The occlusion device 10 is mounted on the distal end of the pusher catheter 14 and is retained in place by the locking mechanism 15. The locking mechanism 15 and the pusher catheter 14 can be used over a guide wire 22.

Overlying the pusher catheter 14 and the occlusion device 10 is the outer sheath 12, which extends to the proximal end of the frame of the occlusion device and in particular into abutment with the dilator tip 20, in order to hold the occlusion device in a compressed condition (as shown in FIG. 2) for delivery. In some embodiments there may be provided other restraining elements to restrain the occlusion device 20 in the sheath, as are known in the art.

The dilator tip 20 protrudes from the distal end of the outer sheath so as to provide a smooth tip to the assembly for navigating through the patient's vasculature to the position at which treatment is required.

In use, a guide wire 22 is introduced into the patient, through their vasculature to the affected vessel, typically by the Seldinger technique. The occlusion device 10, together with the introducer assembly 1, is introduced over the guide wire 22, and follows the path of the guide wire 22 to the affected vessel 40. The occlusion device 10 is able to be introduced over the guide wire 22 by virtue of the lumens 21 and 25. The occlusion device 10 is sealed so as to prevent leakage through the lumen of the device, but so as still to allow the occlusion device to pass over a guide wire, by the seal 32. In the embodiment shown, the seal is provided in the lumen 21 of the dilator tip 20.

Once the occlusion device 10 has been positioned in the correct location in the vessel 40, the outer sheath 14 is withdrawn in a proximal direction in order to expose the occlusion member 28, at which point it expands within the blood vessel 40, as can be seen in FIG. 3. The occlusion member 28 expands to form two conical shapes, the cones extending from their narrowest points away from one another along a generally longitudinal axis of the vessel.

At this stage, the occlusion device 10 is still retained on the distal end of the pusher catheter 14 by means of the locking mechanism 15 engaging with the cannula 24.

In the final stage of deployment, the locking mechanism 15 is disengaged from the cannula 24, and the pusher catheter 12 and the outer sheath 14 are fully withdrawn from the blood vessel leaving only the guide wire 22 and the occlusion device 10 in place. The guide wire 22 may then be withdrawn through the seal and the lumen and out of the patient, leaving only the occlusion device 10, including the cannula and dilator tip, in place (see FIG. 4).

The locking device could in one example include a threaded connection with the cannula 24, a hook or other releasable locking device.

By including a cannula element in the medical device itself, the cannula having a lumen through which a guide wire can pass, the medical device can be introduced over a guide wire into a vessel in a patient. By providing a dilator tip in the medical device itself, the dilator tip also having a lumen through which a guide wire can pass, the whole medical device including the dilator tip can be introduced over a guide wire into a vessel in a patient. By including the dilator tip as part of the medical device, the dilator tip can be left in the patient with the remainder of the medical device; as such there is no need to withdraw the dilator tip through the medical device. By providing a sealing element for sealing the lumen for receiving a guide wire, when the guide wire is removed from the medical device and from the patient, the lumen through the medical device can be sealed so as to prevent fluid flowing therethrough. Where the medical device is an occlusion device, for example, this enables the occlusion device to substantially completely block the vessel as desired.

Figure 5:
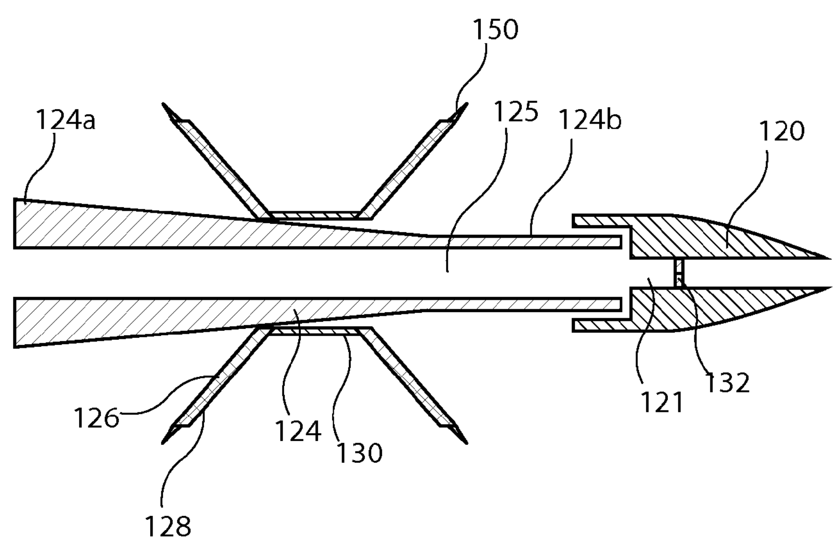
FIG. 5 is a cross-sectional view of an occlusion device having a tapered cannula.

FIG. 5 shows another embodiment of an occlusion device. The occlusion device 100 comprises a cannula 124 having a proximal 124*b* and distal 124*a* end, a dilator tip 120 secured to the proximal end 124*b* of the cannula, and a frame. The frame comprises a central sleeve 130 around the cannula and an occlusion member 128 extending in both directions from the central sleeve 130, the occlusion member covered with graft material 126.

In use, the lumen 125 of the cannula 124 and lumen 121 of the dilator tip 120 pass over the guide wire on introduction into the patient. A seal 132 is provided in the lumen 121 of the dilator tip 120 to prevent leakage around the guide wire and in general through the lumen after the guide wire has been removed. In this embodiment the outer diameter of the cannula 124 tapers from its distal 124*a* to its proximal 124*b* end. The outer diameter of the cannula 124 ranges from smaller than a diameter of the central sleeve 130 to greater than a diameter of the central sleeve 130, such that the relative positions of the cannula 124 and central sleeve 130 can be fixed by forcing the cannula 124 into the central sleeve 130. In this way, during manufacture of the device the cannula 124 can be securely fixed within the central sleeve 130 of the occlusion member by friction. Such a cannula could be retrofitted into various existing occlusion members with different sized central sleeves.

In the embodiment shown in FIG. 5 barbs 150 are provided on the proximal and distal edges of the occlusion member 128. The barbs 150 can assist in fixing the occlusion device in position in the vessel. In some embodiments the barbs 150 on the device may be of a type designed to cause irritation to the wall of the blood vessel, which can provoke tissue in-growth (stenosis). This can assist in providing improved occlusion of the vessel. Of course, the skilled person will understand that the provision of barbs is not essential.

Figure 6:
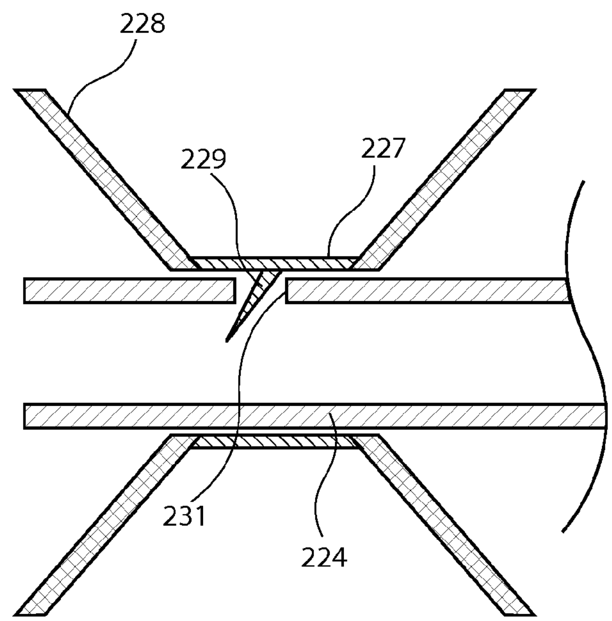
FIG. 6 is a cross-sectional view of an occlusion device having an attachment feature comprising a barb and corresponding hole.

FIG. 6 is a partial cross-sectional view of an occlusion device having an attachment feature 227 comprising a barb 229 on the occlusion member 228 and corresponding hole 231 through the cannula 224. The barb 229 fits through the hole 231 in order to secure the cannula 224 and occlusion member 228 together.

Figure 7:
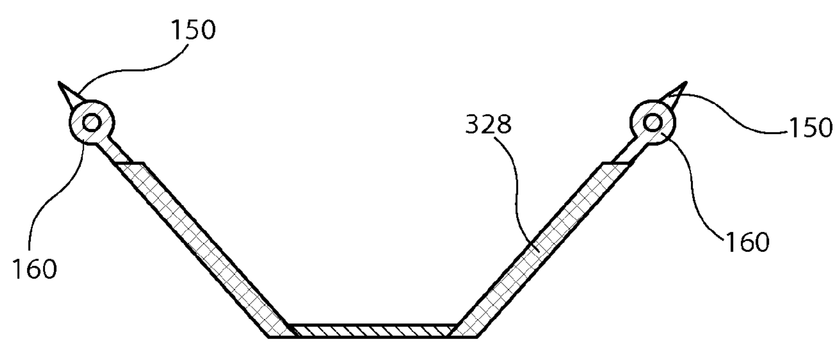
FIG. 7 is a cross-sectional view of part of yet another occlusion device.
Figure 7:
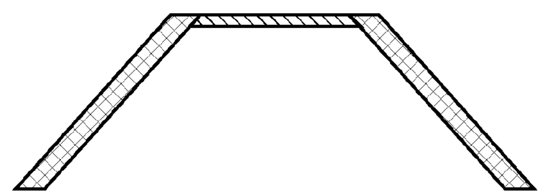

FIG. 7 is a cross-sectional view of yet another occlusion member 328. In the embodiment shown in FIG. 7 radiopaque markers 160 are provided on the proximal and distal edges of the occlusion member 328. The radiopaque markers, of known form, can assist in positioning the occlusion device in the vessel. A barb 150 is provided on the radiopaque markers. Of course, the skilled person will understand that the provision of radiopaque markers is not essential and furthermore that the provision of barbs on the radiopaque markers is not essential.

The skilled person will appreciate that many other modifications can be made to the above-referenced devices.

The frame of the occlusion device could be formed using techniques other than laser cutting. However, laser cutting allows compression of the device back to a very thin tube, which is ideal for delivery.

The frame of the occlusion device need not have an hourglass shape. Instead the frame may comprise only one cone, for example. A single cone would typically be placed with its widest end facing the direction of blood flow.

It is not necessary for the frame of the device to be made from Nitinol. Other shape memory materials could be used, such as other shape memory alloys, or shape memory polymers. Indeed, shape memory materials need not be used at all. Resilient materials such as spring steel could be used. A combination of suitable materials may be used to make the frame.

The graft material membrane is not restricted to being formed from the materials described above. Any suitable graft material could be used. For example, Silicone, Dacron®, Thoralon®, polyurethane, or polyethylene, ePTFE, or a combination of these materials could be used.

Instead of a membrane, fibres could be provided on the frame. These fibres may be silk, a polyamide such as nylon, PET, or electrospun PTFE, for example.

The dilator tip need not be made from polyurethane but may instead be made from a polyamide such as nylon or any other suitable material. The dilator tip and cannula may be a single component. This can reduce the number of steps required in the manufacturing process.

In the embodiment where the cannula tapers from one end to another, the cannula may be wider than the central sleeve of the frame at its proximal end and narrower than the central sleeve at its distal end. In this way the cannula and distal tip could be a single component whilst still allowing the central sleeve of the frame to be forced over the cannula into a fixed arrangement.

The cannula is not restricted to being made from a plastics material such as PEEK. In some embodiments the cannula may be made from metal, such as titanium for example. Titanium has the advantage that it is radiopaque, so the position of the device can be detected and visualised by the surgeon or clinician using X-ray. This can assist in accurate positioning of the device within the vessel.

Instead of or as well as providing a radiopaque cannula, radiopaque markers may be provided on the device to enable visualisation in the vessel and assist with correct positioning of the device within the patient.

The cannula may be secured within the central sleeve of the occlusion member by barbs on one of the cannula and central sleeve. At least one of the cannula and the central sleeve may comprise ribs on their outer and inner surface respectively, to provide a friction fit between the cannula and central sleeve and thus secure the cannula within the central sleeve.

Although the valve is shown as being provided in the lumen of the dilator tip, it may be provided in the lumen of the cannula. The cannula and dilator tip may be a single component and the valve may be provided at any location within the lumen of the single component.

The medical device need not be an occlusion device. In one embodiment, the medical device may be a filter comprising a cannula and a dilator tip having a lumen therethrough which remain with the device after deployment in a vessel, the lumen being sealable. The filter may have an expandable frame member which is able to capture particles and thrombi in the patient's blood stream and prevent them flowing freely through the vessel. Where the medical device is a filter the obstruction member of the frame member is not covered with material but allows fluid to flow through it.

Preferably the device has a diameter slightly larger than that of a vessel into which it is to be located when in its fully expanded configuration.

It is to be understood that the features of the invention described in the dependent claims can be combined with one another in accordance with the teachings above.

The invention claimed is:

1. An implantable medical device for implanting into a vessel, the implantable medical device including:

an expandable frame member for at least partially obstructing a vessel, the expandable frame member including a central sleeve having a cylindrical section;

a cannula element including a first lumen, said cannula element being directly coupled to the cylindrical section, the cannula element having a proximal end and extending to the distal end such that the cannula element has a uniform inner diameter from the proximal end to the distal end;

a dilator tip including a second lumen, said dilator tip being located at one of the proximal end and distal end of the cannula element, the cannula element being disposed within the dilator tip;

wherein one of the cannula element and the dilator tip is provided with a seal for sealing one of the first lumen and the second lumen.

2. An implantable medical device according to claim 1, wherein the frame member is collapsible to lie substantially parallel to the cannula element.

3. An implantable medical device according to claim 1, wherein the frame member is expandable to a deployed configuration wherein at least a part of the frame member extends radially from the cannula element.

4. An implantable medical device according to claim 3, wherein in the deployed configuration at least a part of the frame member extends radially from and longitudinally along the cannula element so as to form at least one substantially conical shape.

5. An implantable medical device according to claim 3, wherein in the deployed configuration the frame member includes first and second portions which each extend radially from and longitudinally along the cannula element away from one another so as to form a substantially hourglass shape.

6. An implantable medical device according to claim 1, wherein the implantable medical device is an occlusion device and wherein at least a part of the frame member is covered with occlusion material.

7. An implantable medical device according to claim 1, wherein the seal includes a valve.

8. An implantable medical device according to claim 7, wherein the valve is a cross-slit valve.

9. An implantable medical device according to claim 1, wherein the cannula element is coupled concentrically within the central sleeve of the frame member.

10. An implantable medical device according to claim 1, wherein the cannula is fixed within the central sleeve by friction.

11. An implantable medical device according to claim 1, wherein the central sleeve is made from a shape memory material.

12. An implantable medical device according to claim 11, wherein the central sleeve is made from Nitinol.

13. An implantable medical device according to claim 1, wherein the cannula element is formed from a polymer, metal or metal alloy.

14. An implantable medical device according to claim 13, wherein the cannula element is made from a shape memory material.

15. An implantable medical device according to claim 13, wherein the cannula element is made from Nitinol.

16. An implantable medical device according to claim 1, wherein the cannula element and the dilator tip member are fixed to one another.

17. An implantable medical device according to claim 1, wherein the cannula element and the dilator tip member are formed of a single piece.

18. An implantable medical device according to claim 1, comprising at least one of a radiopaque marker and a barb for fixing the occlusion device in position in the vessel.

19. An implantable medical device according to claim 1, wherein the implantable medical device is a filter.

20. An implantable medical device for implanting into a vessel, the implantable medical device including:

an expandable frame member for at least partially obstructing a vessel, the frame member including a central sleeve;

a cannula element including a first lumen, said cannula element being coupled within the frame member, the cannula element being attached to the central sleeve of the frame member, wherein the cannula element has a tapered outer diameter, said outer diameter ranging from smaller than a diameter of the central sleeve to greater than a diameter of the central sleeve, such that the relative positions of the cannula and central sleeve can be fixed by forcing the cannula into the central sleeve;

a dilator tip including a second lumen, said dilator tip being located at an end of the cannula element;

wherein one of the cannula element and the dilator tip is provided with a seal for sealing one of the first lumen and the second lumen.

21. An implantable medical device for implanting into a vessel, the implantable medical device including:

an expandable frame member for at least partially obstructing a vessel, the frame member includes a central sleeve wherein the central sleeve is provided with at least one inwardly extending barb for fixing the location of the central sleeve relative to the cannula element;

a cannula element including a first lumen, said cannula element being coupled within the frame member;

a dilator tip including a second lumen, said dilator tip being located at an end of the cannula element;

wherein one of the cannula element and the dilator tip is provided with a seal for sealing one of the first lumen and the second lumen.

* * * * *